United States Patent
Park et al.

(10) Patent No.: US 8,992,830 B2
(45) Date of Patent: Mar. 31, 2015

(54) HIGH TEMPERATURE DECONTAMINATION OF AIRCRAFT COMPARTMENTS

(71) Applicant: The Boeing Company, Chicago, IL (US)

(72) Inventors: Shawn Hyunsoo Park, Cerritos, CA (US); Leora Peltz, Pasadena, CA (US); Rovelyn Tapec Dytioco, Seattle, WA (US); Conor James Van Camp, Long Beach, CA (US)

(73) Assignee: The Boeing Company, Chicago, IL (US)

( * ) Notice: Subject to any disclaimer, the term of this patent is extended or adjusted under 35 U.S.C. 154(b) by 60 days.

(21) Appl. No.: 13/843,389

(22) Filed: Mar. 15, 2013

(65) Prior Publication Data

US 2014/0271347 A1 Sep. 18, 2014

(51) Int. Cl.
*A61L 9/00* (2006.01)
*G05B 1/00* (2006.01)
(Continued)

(52) U.S. Cl.
CPC ... *A61L 2/22* (2013.01); *A61L 2/06* (2013.01); *B64D 13/08* (2013.01); *B64F 5/0018* (2013.01); *A61L 2202/25* (2013.01)
USPC ............ 422/28; 422/1; 422/3; 422/4; 422/34; 422/62; 422/105; 454/156; 454/159; 239/3

(58) Field of Classification Search
CPC ........... A61L 9/00; A61L 9/015; A61L 9/032; A61L 9/145; F24F 13/28; B01F 5/20
USPC ................... 422/1, 3, 5, 28, 34, 62, 105, 298, 422/305–306; 454/139, 156–157, 159, 228; 95/10, 25; 96/52–53, 223, 226–227, 96/242–243, 413, 417; 239/3
See application file for complete search history.

(56) References Cited

U.S. PATENT DOCUMENTS 6,692,694 B1  2/2004  Curry et al.
2005/0074359 A1  4/2005  Krieger et al.
(Continued)

FOREIGN PATENT DOCUMENTS

DE  202009018034 U1  12/2010
WO  03080132 A1  10/2003

OTHER PUBLICATIONS

Mundis, Chris, et al., "Hot Air Decontamination of the C-141 Aircraft Technology Development Program", Battelle Eastern Science and Technology Center, Apr. 2004, Retrieved from the Internet: < http://www.dtic.mil/cgi-bin/GetTRDoc?AD=ADA426211 >, 23 pgs.

(Continued)

*Primary Examiner* — Monzer R Chorbaji
(74) *Attorney, Agent, or Firm* — Kwan & Olynick LLP

(57) ABSTRACT

Provided are methods for decontamination of compartments, such as aircraft compartments and other types of compartments, and systems for implementing these methods. In some embodiments, a method involves detecting presence of one or more contaminants in a compartment. This information is used to select various decontamination conditions. In some embodiments, additional information, such as the type of the compartment (e.g., an aircraft compartment), temperature, and humidity, may be also considered while selecting the decontamination conditions. The decontamination conditions include identification of one or more decontaminating agents to be dispensed in the compartment, temperature profile of the air to be flown into the compartment, and timing of the decontaminant dispensing and air flowing operations. These conditions are selected to increase efficacy of the selected decontaminating agents with respect to the one or more detected contaminants and reduce impact on the aircraft compartment.

16 Claims, 7 Drawing Sheets

(51) Int. Cl.
  *B60H 3/00* (2006.01)
  *A01G 23/10* (2006.01)
  *A61L 2/22* (2006.01)
  *A61L 2/06* (2006.01)
  *B64D 13/08* (2006.01)
  *B64F 5/00* (2006.01)

(56) References Cited

U.S. PATENT DOCUMENTS

2007/0098592 A1    5/2007    Buezynski et al.
2007/0217944 A1*   9/2007    Potember et al. .................. 422/4
2009/0053989 A1*   2/2009    Lunde et al. ................... 454/187
2010/0189599 A1*   7/2010    Bobbert ......................... 422/28
2011/0171065 A1    7/2011    Park et al.
2012/0273584 A1   11/2012    Peltz et al.

OTHER PUBLICATIONS

"European Application Serial No. 14158770.9, Search Report mailed Jun. 16, 2014", 9 pgs.

* cited by examiner

HIGH TEMPERATURE DECONTAMINATION OF AIRCRAFT COMPARTMENTS

FIELD

This invention relates to decontamination of compartments and, more specifically, to methods and systems of high temperature decontamination of aircraft compartments using low-concentration decontaminating agents.

BACKGROUND

Infectious diseases may be introduced into vehicles, including commercial and military aircrafts. With the growing popularity of air travel and new destinations, the potential for transmission of the infectious diseases has increased. In particular, the prevalence of air travel between the continents has increased the potential and created local "hot spots." The transmission of infectious diseases may be controlled to a certain extent by air filtration and recirculating air in aircraft compartments as well as wiping exposed surfaces with disinfecting agents. However, these methods can be not fully effective, costly, time consuming, or have other unintended results. For example, many modern aircrafts cannot be thoroughly wiped during their short landing periods. Furthermore, some exposed surfaces, such as narrow channels and openings, may not be sufficiently accessible for wiping. Other techniques, such as filling the aircraft compartment with concentrated hydrogen peroxide or humid air at high temperatures are slow and may have unintended effects on the aircrafts.

SUMMARY

Provided are methods for decontamination of compartments, such as aircraft compartments and other types of compartments, and systems for implementing these methods. In some embodiments, a method involves detecting presence of one or more contaminants in a compartment. This information is used to select various decontamination conditions. In some embodiments, additional information, such as the type of the compartment (e.g., an aircraft compartment), temperature, and humidity, may be also considered while selecting the decontamination conditions. The decontamination conditions include identification of one or more decontaminating agents to be dispensed in the compartment, temperature profile of the air to be flown into the compartment, and timing of the decontaminant dispensing and air flowing operations. These conditions are selected to increase efficacy of the selected decontaminating agents with respect to the one or more detected contaminants and reduce impact on the aircraft compartment.

In some embodiments, a method for decontamination of a compartment may commence with detecting presence of one or more contaminants in the compartment. Some examples these contaminants include target pathogens and bio-agents. The detection may be performed automatically using, for example, one or more sensors on a decontamination system. Alternatively, manual detection may be used. In some embodiments, concentrations and/or other characteristics of these contaminants may be detected in this operation in addition to identification of particular contaminants. Some examples of the compartments include aircraft compartments.

The method may proceed with selecting decontamination conditions for use in the compartment. The decontamination conditions are selected based on the presence of the one or more contaminants in the compartment and characteristics of these contaminants. In some embodiments, other information is also used for selecting the decontamination conditions, such as the type of the aircraft (e.g., passenger or cargo), size of the aircraft, temperature and/or humidity levels inside and/or outside of the aircraft, and the like. The decontamination conditions may include at least identification of a decontaminating agent (e.g., chemical name) for dispending, identification of an operating temperature of a heated air for flowing through the compartment during the decontamination, and relative timing of the dispensing and flowing operations. Other decontamination conditions may be selected as well, such as temperature profiles or more specifically temperature transition profiles, one or more humidity levels inside the compartment during the decontamination, instructions to repeat one or more operations, and the like. The operating temperature of the airflow may be optimized for a specific decontaminating agent that is selected as well as for one or more detected contaminants. As such, efficacy of the decontaminating agent with respect to the detected contaminants in improved. Furthermore, the operating temperature may be optimized in order to reduce corrosion of the compartment.

The method may proceed with dispensing the decontaminating agent in an aerosolized form in the compartment as well as flowing the heated air through the compartment. The air is heated to the selected operating temperature. In some embodiments, the dispensing operation precedes the flowing operation. Alternatively, the dispensing operation may follow the flowing operation. In some embodiments, the dispensing operation and/or the flowing operation are repeated one or more times. For example, the air may be initially flown into the compartment at a certain temperature to stimulate germination of detected spores. The air may be flown for a period of time before the decontaminating agent is dispensed in the compartment, which allows the spores to germinate before coming in contact with the decontamination agent. The germinating spores are significantly less resilient than intact spores (i.e., the spores that have not gone through the germination process) and, as a result, a less concentrated decontaminating agent may still be effectively used. If the spores were not allowed to geminate, a more concentrated decontamination agent may be needed.

After the decontaminating agent is dispensed, the temperature of the air flown through the compartment may be increased to a higher level. The temperature transition may be specifically controlled to ensure high efficacy of the decontaminating agent with respect to the detected contaminants, such as the spores in the above example. As the temperature increases, the efficacy of the decontaminating agent also increases until evaporation and dissociation of the decontaminating agent (caused by the heat) start suppressing the efficacy of the decontaminating agent. The corrosive properties of the decontaminating agent are also suppressed because of the evaporation and dissociation, and the decontaminating agent is at least partially removed from the compartment by this airflow.

In some embodiments, the selected operating temperature is between about 100 degrees Fahrenheit and 180 degrees Fahrenheit or, more specifically, between about 120 degrees Fahrenheit and 140 degrees Fahrenheit. As noted above, the operating temperature is selected to increase efficacy of the decontaminating agent with respect to the one or more detected contaminants and to reduce corrosion of the compartment. In some embodiments, the operating temperature is selected to minimize duration of the heated air flowing through the compartment. The operating temperature may be also selected to minimize a concentration of the decontaminating agent.

In some embodiments, the decontaminating agent includes hydrogen peroxide and/or acetic acid. The concentration of hydrogen peroxide in the decontaminating agent may be less than 1% by weight or, more specifically, less than 0.1% by weight or even less than 0.01% by weight. The concentration of acetic acid may be less than 1% by weight or, more specifically, less than 0.5% by weight or even less than 0.05% by weight. As noted above, the decontaminating agent is dispensed in the aerosolized form such that droplets are between about 1 micron and 20 microns in size.

In some embodiments, the decontamination conditions also include a temperature ramping profile. The temperature ramping profile may be linear or have some other shape, such as an exponential increase profile. The decontamination conditions may include a relative humidity of the heated air flowing through the compartment. The relative humidity of the heated air may be between 40% and 80% or, more specifically, about 60%.

In some embodiments, the method also involves providing a decontamination system that includes a decontaminating agent dispenser, an air heater, an air blower, and a controller. The controller is configured to determine the decontamination conditions. At least a portion of the decontamination system may be integrated into the aircraft. For example, the air heater and the air blower may be a part of the aircraft ventilation system. In the same or other embodiments, at least a portion of the decontamination system may be separate from the aircraft. For example, the decontaminating agent dispenser may be brought to the aircraft during the decontamination process. In some embodiments, the decontamination system also includes one or more sensors for determining presence of the one or more contaminants.

Provided also is a system for decontamination of the compartment. The system includes a controller for selecting decontamination conditions for use in the compartment. The decontamination conditions are selected based on presence of one or more contaminants, such as target pathogens and bioagents. The decontamination conditions include at least identification of a decontaminating agent for dispending in an aerosolized form in the compartment. Other decontamination conditions may include identification of an operating temperature of a heated air for flowing through the compartment during the decontamination and/or relative timing of dispensing the decontaminating agent and flowing the heated air. The operating temperature is selected to increase efficacy of the decontaminating agent with respect to the one or more contaminants and to reduce corrosion of the compartment. The decontamination system also includes a decontaminating agent dispenser for dispensing the decontaminating agent in the aerosolized form in the compartment. Other components of the decontamination system may include an air heater for heating the air to the operating temperature and/or an air blower for flowing the heated air through the compartment.

The features and functions that have been discussed can be achieved independently in various embodiments or may be combined in yet other embodiments further details of which can be seen with reference to the following description and drawings.

DETAILED DESCRIPTION

Figure 1A:
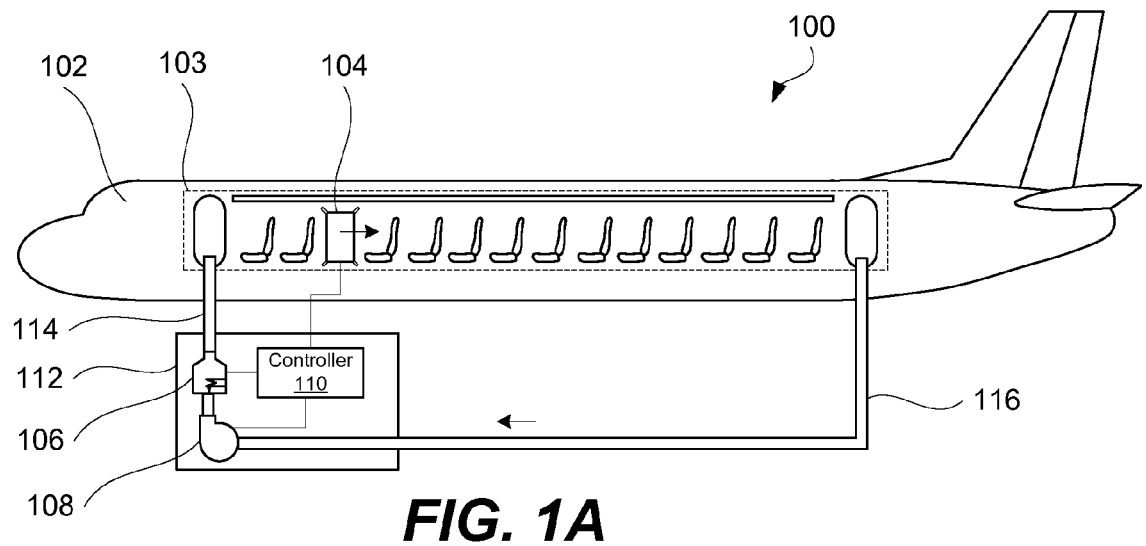
FIGS. 1A-1C are schematic representations of various decontamination systems that are connected to and/or integrated into respective aircrafts, in accordance with some embodiments.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.
Introduction Vehicles, including aircrafts, can get contaminated with various biological pathogens (natural or man-made) and other types of undesirable contaminants. Aircrafts or, more specifically, aircraft compartments need to be decontaminated as a part of the periodic service or when a specific contaminant is suspected or detected.

Various decontamination methods have been proposed in the past but proved to be slow, costly, not fully effective, or have unintended results on the aircrafts. For example, commercial aircrafts are currently required to go through periodic wipe-downs, which involve wiping of exposed surfaces in passenger compartments with a decontaminating agent. While adopted as an industry standard, this method is very labor intensive and may not be fully effective. Many hidden surfaces and small cavities remain unattended and can retain substantial amounts of contaminants. Furthermore, many biological pathogens are quite resilient at room temperatures and require concentrated harsh chemicals, such as peroxides and/or acids. The chemicals at required high concentration can have an impact on the aircrafts. Certain types of aircrafts are subjected to hot-air decontamination using dry or humid air (e.g., 80-90% relative humidity) maintained at temperature of 180 degrees Fahrenheit for 48-72 hours. Not only this method is very slow, but it may cause various undesirable effects. Specifically, vapor in the air can condensate on surfaces and penetrate into crevices causing corrosion.

It has been found that certain combinations of decontaminating conditions may affect various types of biological pathogens in different ways. For example, anthrax spores respond differently than a severe acute respiratory syndrome coronavirus when, for example, subjected to a hot humid air. Current decontamination methods rarely account for different types of contaminants and instead use the same general cleaning procedure for all different types of contaminants. As a result, these methods require very harsh conditions in order to deal with a number of different types of contaminants, such as highly concentrated chemicals. As noted above, these harsh conditions may not be fully effective in some situations, e.g., specific kind of biological pathogens that may require a unique set of conditions that falls outside of the general protocol Provided are methods for decontamination of aircraft compartments from different types of contaminants, such as target pathogens and bio-agents. Also provided are systems for implementing these methods. In some embodiments, the methods are designed to detect presence of specific contaminants in the aircraft compartments and select decontamination conditions suitable and tailored specifically for these detected contaminants. In other words, certain specific vulnerabilities of the detected contaminants are accounted for. For example, one set of decontamination conditions may be used for anthrax spores, while another set may be used for severe acute respiratory syndrome coronavirus. This tailored approach allows more effective decontamination without a need for unnecessary harsh conditions, such as concentrated chemicals, high humidity, long exposure times, and the like. Furthermore, the decontamination duration can be reduced to a few hours and, in some embodiments, to a few minutes, while still providing effective results.

The selected decontamination conditions include identification of a specific decontaminating agent for dispensing into aircraft cabin, identification of an operating temperature of the hot air for flowing into the aircraft compartment, and relative timing of the dispensing and flowing operations. Other conditions may be selected as well, such as humidity of the air flowing into the aircraft compartment, and the like. A combination of decontaminating agents and heated air used in the same decontamination process may be referred to as integrated hot air decontamination (IHAD). This combination allows shortening the duration of the decontamination process and reducing the concentration of the decontaminating agents. For example, a conventional decontamination process that uses hydrogen peroxide at a room temperature requires at least 30% by weight concentration of hydrogen peroxide in order to achieve effective decontamination. At this concentration, hydrogen peroxide is extremely corrosive. At the same time, raising the temperature to between about 100 degrees Fahrenheit and 180 degrees Fahrenheit allows reducing the hydrogen peroxide concentration to less than 1% by weight and even to less than 0.01% by weight while still providing effective decontamination. In other words, efficacy of many decontaminating agents may be greatly enhanced by raising the temperature of the environment that is being decontaminated. Furthermore, the temperature and, in some embodiments, humidity of the air in the aircraft compartment may be used to control evaporation of the dispensed decontaminating agent and thereby control exposure of the surfaces to the agent and prevent or at least minimize corrosive effects of the agent. As such, the flow of heated air may be used to evaporate and/or dissociated the dispensed agent in the aircraft compartment.

In some embodiments, the flow of heated air may be used to supply some or most (if not all) of the decontaminating agent into the aircraft compartment. For example, some amount of the decontaminating agent may be dispensed, while the remaining decontaminating agent may be introduced into the air flow. In some embodiments, the entire amount of the decontaminating agent is introduced into the air flow.

The one or more selected decontaminating agents may be prepared on-site by the decontamination system itself. For example, the system may include a number of chemicals (e.g., peroxides and acids) that are combined together according to a formulation of the selected decontaminating agent. A specific example, involves adjusting the concentrating of the decontaminating agent in situ.

The one or more decontaminating agents may be dispensed in the aircraft compartment in the aerosolized form with a droplet size of between about 1 micron and 20 microns. Small droplets are capable of reaching hidden areas in the aircraft compartment, such as crevices and more thoroughly decontaminate detected contaminants. Furthermore, the aerosolized form may help with more uniform distribution of the agent throughout the aircraft compartment as the droplets can be carried by the air flow for long distances before contacting surfaces within the air craft compartment.

The dispensing and air flowing operations may be specifically timed to achieve effective decontamination. A brief example of spore decontamination may help to further illustrate this timing feature. Once the presence of certain spores is detected in the aircraft compartment and specific conditions are selected for decontamination of these spores, the process may proceed with dispensing a decontaminating agent at an initial concentration. During this dispensing, the temperature inside the aircraft compartment may be maintained at a certain initial elevated level by, for example, flowing a heated air. In some embodiments, no initial dispensing of the decontaminating agent is performed, and the heated air is flown for a period of time before any decontaminating agent is introduced into the compartment. A combination of these initial conditions may be specifically selected to stimulate germination of the spores since the germinating spores are significantly less resilient to decontaminating agents than the intact spores. After a certain period of time that allows some germination to occur, the decontaminating agent is dispensed. As noted above, this may be the first time or the second time the decontaminating agent is dispensed in the aircraft compartment. The temperature may be increased (e.g., after some further delay) to a higher level. The temperature profile (e.g., the delay and/or the increase from one level to another) may be selected to increase efficacy of the decontaminating agent with temperature. As the temperature increases, the potency of the decontaminating agent is enhanced until the effects of evaporation and dissociation set in. The temperature is maintained at this new elevated level to evaporate the decontaminating agent, which may have condensed on the surfaces and in crevices.

The decontamination conditions are selected based on the presence of the one or more contaminants in the aircraft compartment. Other parameters can be used as well, such temperature and/or humidity of the aircraft compartment, environmental conditions outside of the aircraft compartment, type of the aircraft (e.g., cargo, commercial, size of the aircraft), time constraints, and the like. Furthermore, the decontamination system may use other general information, such information about efficacy of different decontaminating agents on various contaminants, aircraft materials, and the like. This information may be stored in a database of the decontamination system and/or supplied to the system prior to or during the decontamination system. For example, a new contaminant may be detected and the decontamination system or an operator may contact an outside database for additional information about this contaminant.

Some decontamination operations may be repeated using the same or new conditions. For example, the temperature of the air may be changed one or more times during the overall process. Likewise, the dispensing operation may be repeated one or more times using the same or different decontaminating agents (e.g., different concentrations). Furthermore, the system may have various feedback control loops in order to maintain conditions (e.g., temperature, humidity, agent concentration) in the aircraft compartment at desired levels.

It should be noted that the contaminant detection, selection of specific conditions, and decontamination using these conditions can be mostly completed at the aircraft. In some embodiments, parts of the decontamination system may be integrated into an aircraft and/or certain aircraft components, such as a ventilation system, may be used in the decontamination process. More specifically, most if not all components of the decontamination system may be integrated into aircraft. In these embodiments, the aircraft may perform decontamination without being connected to any external components. The decontamination may be performed while the aircraft is on the ground (e.g., when the aircraft compartment is vacant) and, in some instanced, when the aircraft is flying.

While the following description references an aircraft, it should be appreciated that the subject matter described herein may be applicable to any types of vehicles, objects, or areas. For example, the subject matter described herein could just as readily be applied to decontaminate of an automotive vehicle, a building, and/or any other area that is at least potentially contaminated. Accordingly, any reference to the "aircraft" throughout the following description is merely meant to illustrate one potential application of the teachings of the subject matter described herein.

As used herein, the term "decontaminating" refers to removing, inactivating, and/or destroying a pathogen on a surface and/or item such that the pathogen is no longer capable of transmitting infectious particles and such that the surface and/or item is rendered safe for handling, use, and/or disposal. The term "pathogen" refers to any disease, illness, and/or infection-producing agent including, without limitation, a germ, a virus, a bacterium, a protozoon, a fungus, and/or a microorganism.

As used herein, an element or step recited in the singular and proceeded with the word "a" or "an" should be understood as not excluding plural elements or steps unless such exclusion is explicitly recited. Furthermore, references to "one embodiment" of the or the "exemplary embodiment" are not intended to be interpreted as excluding the existence of additional embodiments that also incorporate the recited features.

Decontamination System Examples

Figure 1B:
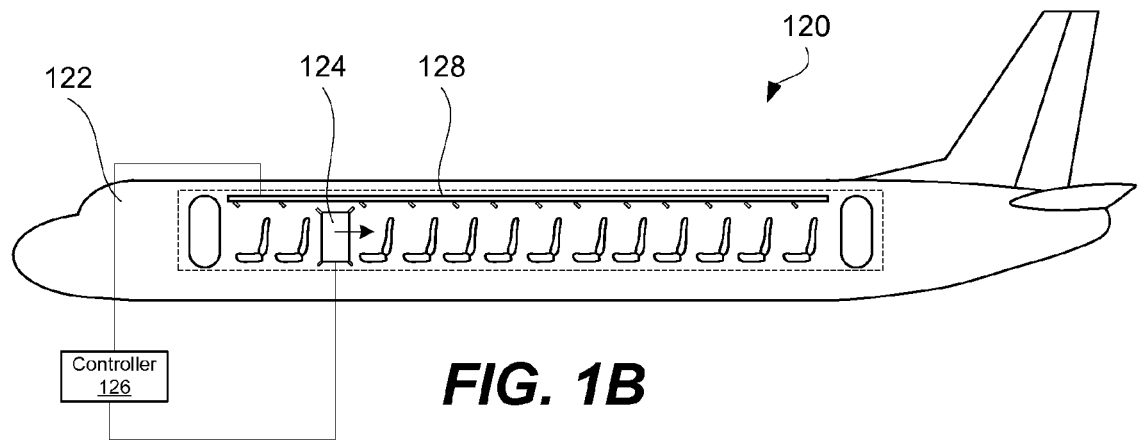
Figure 1C:
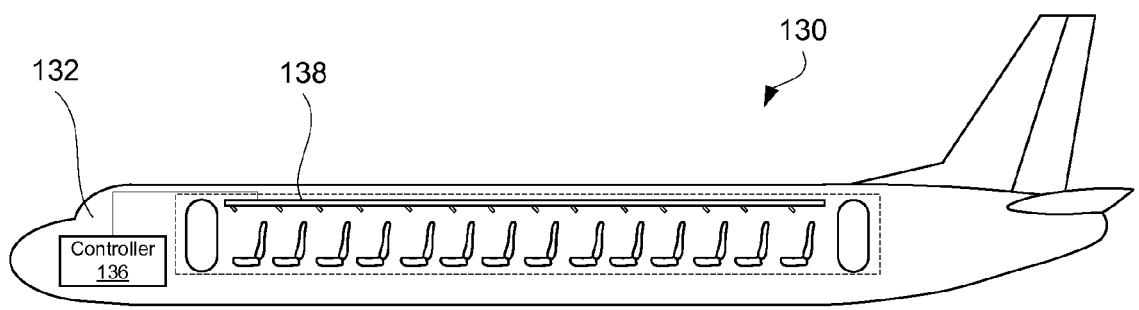

FIGS. 1A-1C are schematic representations of different decontamination systems 100, 120, and 130, in accordance with some embodiments. FIG. 1A illustrates an example of a standalone decontamination system 100 connected to aircraft 102 during its operation. Decontamination system 100 includes a decontaminating agent dispenser 104, an air heater 106, an air blower 108, and a controller 110. Decontamination system 100 may include other components or fewer components. For example, air heater 106 and air blower 108 may be integrated into a single component. Alternatively, a decontamination system may utilize an aircraft ventilation system for heating the air, flowing the heated air through an aircraft compartment, and in some embodiments, even dispense the decontamination agent as further described in FIGS. 1B and 1C. In some embodiments, the decontamination system also includes a filtration component for capturing contaminants and decontaminating agents removed from the aircraft.

Figure 3:
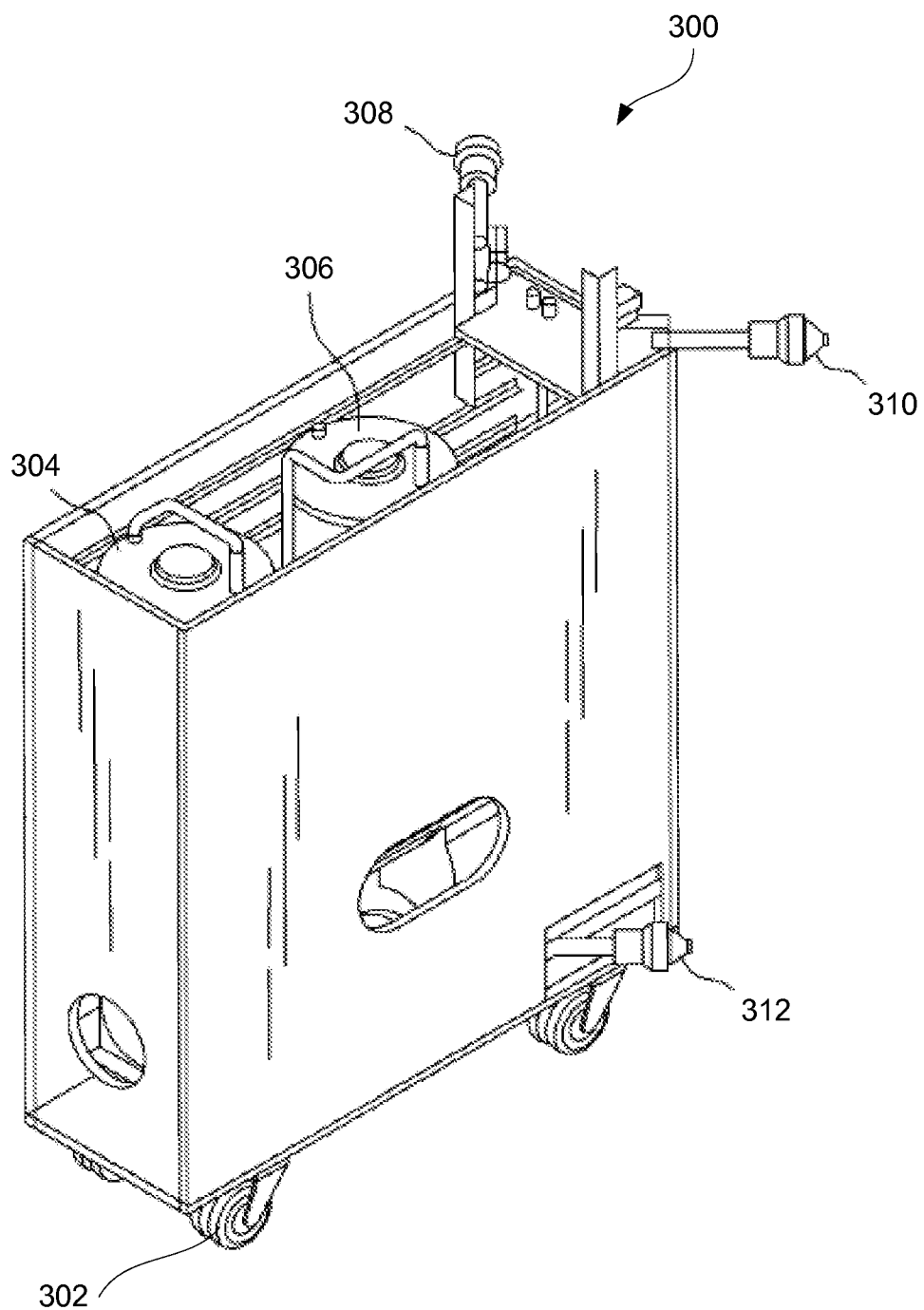
FIG. 3 is a schematic representation of a decontaminating agent dispenser, in accordance with some embodiments.

Returning to FIG. 1A, decontaminating agent dispenser 104 is used for dispensing a decontaminating agent in an aerosolized form in an aircraft compartment 103. This decontaminating agent dispenser 104 may be brought to aircraft 102 during its decontamination and, in some embodiments, stored within aircraft 102. One example of decontaminating agent dispenser 104 is illustrated in FIG. 3. Decontaminating agent dispenser 300 may include a wheeled platform 302 sized to fit inside the aircraft and through the aircraft openings, such as aircraft doors. Dispenser 300 may also include one or more tanks operable to contain one or more decontaminating agents and/or solvents (e.g., hydrogen peroxide and water). FIG. 3 illustrates two tanks 304 and 306, for example, tank 304 used for a decontaminating agent, while tank 306 is used for solvent (e.g., water) to dilute the decontaminating agent. However, any number of tanks can be used. This number may depend on number of different chemicals and/or solvents used to formulate decontaminating agents and various different formulations that dispenser 300 can provide. In some embodiments, dispenser 300 includes only one tank and the specific formulation of the decontaminating agent is prepared outside of dispenser 300. One or more tanks are supported by wheeled platform 302.

Dispenser 300 may also include one or more nozzles for distribution of the decontaminating agents. FIG. 3 has three visible nozzles 308, 310, and 312. However, any number of nozzles may be used: one, two, three, four, six, eight, etc. Nozzles 308, 310, and 312 may have fixed pre-determined direction or may be movable nozzles that change their orientations with respect to other components of dispenser 300 during the dispensing operation. For example, if dispenser 300 is used in an aisle of a passenger plane, then two nozzles may be pointed under the seats while two additional nozzles may be pointed above the seats (one on each side of the aisle). In some embodiments, two additional nozzles may be pointed to overhead luggage compartments. An electrostatic charging system may be connected to one or more nozzles for applying an electrostatic charge to the decontaminating agents as the agents are dispersed. The electrostatic aspect of the spray nozzles results in the dispersion of the charged decontaminating agent, which causes the particles to adhere to the various surfaces, for example, within the aircraft thereby reduced the amount of time the particles are suspended in the compartment.

Dispenser 300 may also include one or more compressors for pressurizing the decontaminating agents. The one or more compressors are capable of supplying a pressure sufficient for a constant distribution of the decontaminating agents through the nozzles. In some embodiments, dispenser 300 has a size similar to an existing aircraft service/food cart, which allows for storage within the aircraft (replacing one of the service/food carts).

Returning to FIG. 1A, air heater 106 is used for heating the air to an operational system determined by controller 110. In some embodiments, air heater 106 is configured to heat the air to a temperature of between about 100 degrees Fahrenheit and 180 degrees Fahrenheit or, more specifically, between about 100 degrees Fahrenheit and 180 degrees Fahrenheit. Various electrical and other types of heaters may be used for this purpose. Air blower 108 force the heated air through aircraft compartment 103. The air flow rate may be determined by controller 110 and may be a function of the compartment size, air temperature, and other factors. Air heater 106 and air blower 108 may be positioned outside of aircraft 102 and connected to aircraft 102 by a supply duct 114. The air may be removed from aircraft 102 and directed into return duct 116 connected to air heater 106 and air blower 108. In some embodiments, a filtration unit (not shown) is connected to return duct 116 to remove contaminants and/or decontaminating agents from the air before returning it back to aircraft 102. In some embodiments, some or most (if not all) decontaminating agent is dispensed into the airflow. For example, dispenser 104 may be integrated into supply duct 114.

Controller 110 is used to select decontamination conditions as further described below. These conditions are selected based on detecting presence of particular contaminants in the aircraft compartment and may include an operating temperature of the heated air supplied by air heater 106 as well as a composition and other characteristics of one or more decontaminating agents dispensed by decontaminating agent dispenser 104. Controller 110 may be integrated with air heater 106 and air blower 108 into an external unit 112 as shown in FIG. 1A. Controller 110 is communicatively coupled to dispenser, air heater 106, and air blower 108 as will now be described with reference to FIG. 2.

Figure 2:
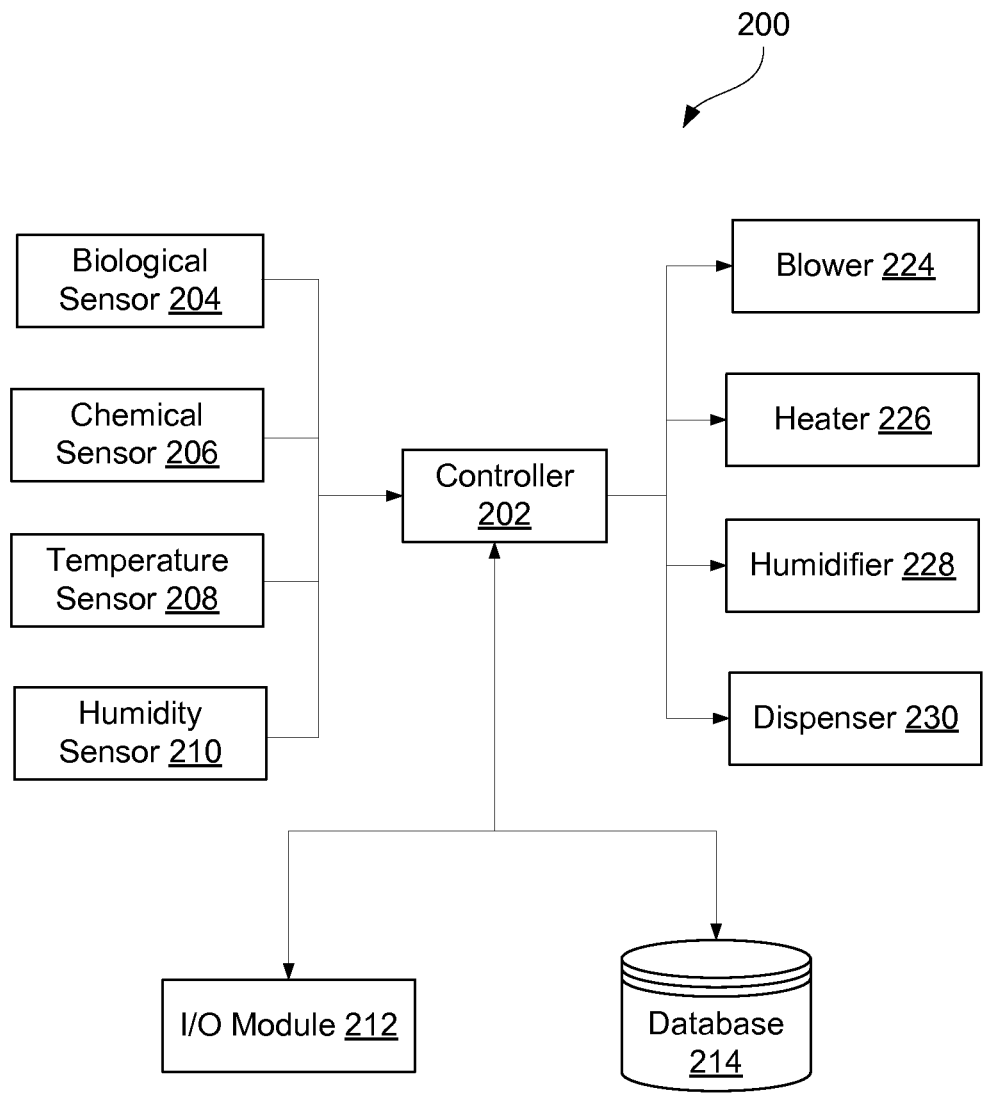
FIG. 2 is a schematic representation of information flows between various components of a decontamination system, in accordance with some embodiments.

FIG. 2 is a schematic representation of information flowing among various components of a decontamination system 200, in accordance with some embodiments. Decontamination system 200 includes a number of input components, such as biological sensor 204, chemical sensor 206, temperature sensor 208, and humidity sensor 210. Other types of sensors may be used as well. In some embodiments, biological sensor 204 includes a bio-recognition component and a bio-transducer component. The recognition component, such as a bio-receptor, may use biomolecules to interact with the analyte of interest. This interaction may be measured by the bio-transducer, which outputs a measurable signal proportional to the presence of the target analyte in the sample. Some examples of chemical sensor 206 include a catalytic bead sensor, chemical field-effect transistor, electrochemical gas sensor, infrared point sensor, and ion-selective electrode. Examples of temperature sensor 208 include an infrared thermometer, resistance thermometer, thermistor, and thermocouple. A hygrometer or a humistor may be used humidity sensor 210.

The input components provide information to controller 202 about the environment within the aircraft compartment and outside of the compartment. For example, biological sensor 204 and chemical sensor 206 may be used for detection of contaminants in the compartment and provide information about the detected contaminants to controller 202. Temperature sensor 208 and humidity sensor 210 may be used to measure temperature and humidity, respectively, inside the aircraft compartment and outside of the compartment. For example, one thermocouple may be positioned in the aircraft compartment, while another thermocouple may be positioned outside of the compartment. Additional thermocouples may be positioned in the supply air duct and the exhaust air duct. Furthermore, multiple thermocouples may be positioned throughout the aircraft compartment, particularly in the locations that are expected to experience high and low temperatures.

Controller 202 may also receive information from input/output module 212 and/or database 214. In some embodiments, controller 202 is integrated with input/output module 212 and/or database 214 into one computer system. Various examples and features of computer systems are described below with reference to FIG. 7.

Controller 202 is configured to select decontamination conditions for use in the aircraft compartment based on presence of one or more contaminants and other information, e.g., information provided from various sensors, from input/output module 212 and/or database 214. Once controller 202 selects the decontamination conditions, these conditions are sent to various components of decontamination system 200 responsible for implementing these conditions in the aircraft compartment. These components may include an air blower 224, an air heater 226, a humidifier 228, and a decontaminating agent disperser 230.

Returning to FIGS. 1B and 1C, some parts of the decontamination system or the entire decontamination system may be integrated into an aircraft. FIG. 1B illustrates an example of decontamination system 120 that includes a disperser 124 and a controller 126. Heated air is supplied by ventilation system 128, which is a part of aircraft 122 in this example. Controller 126 may be communicatively coupled to ventilation system 128 to provide instructions about timing, temperature, airflow, and other conditions. FIG. 1C illustrates another example of decontamination system 130 that is fully integrated into aircraft 132. Decontamination system 130 includes controller 136, which is positioned on board of aircraft 132 and may be integrated into other controllers of aircraft 132. Controller 136 may direct operation of ventilation system 138 at least during the decontamination process. Dispensing of a decontaminating agent may be performed through ventilation system 138 or an on-board dispenser (not shown).

Decontamination Method Examples

Figure 4:
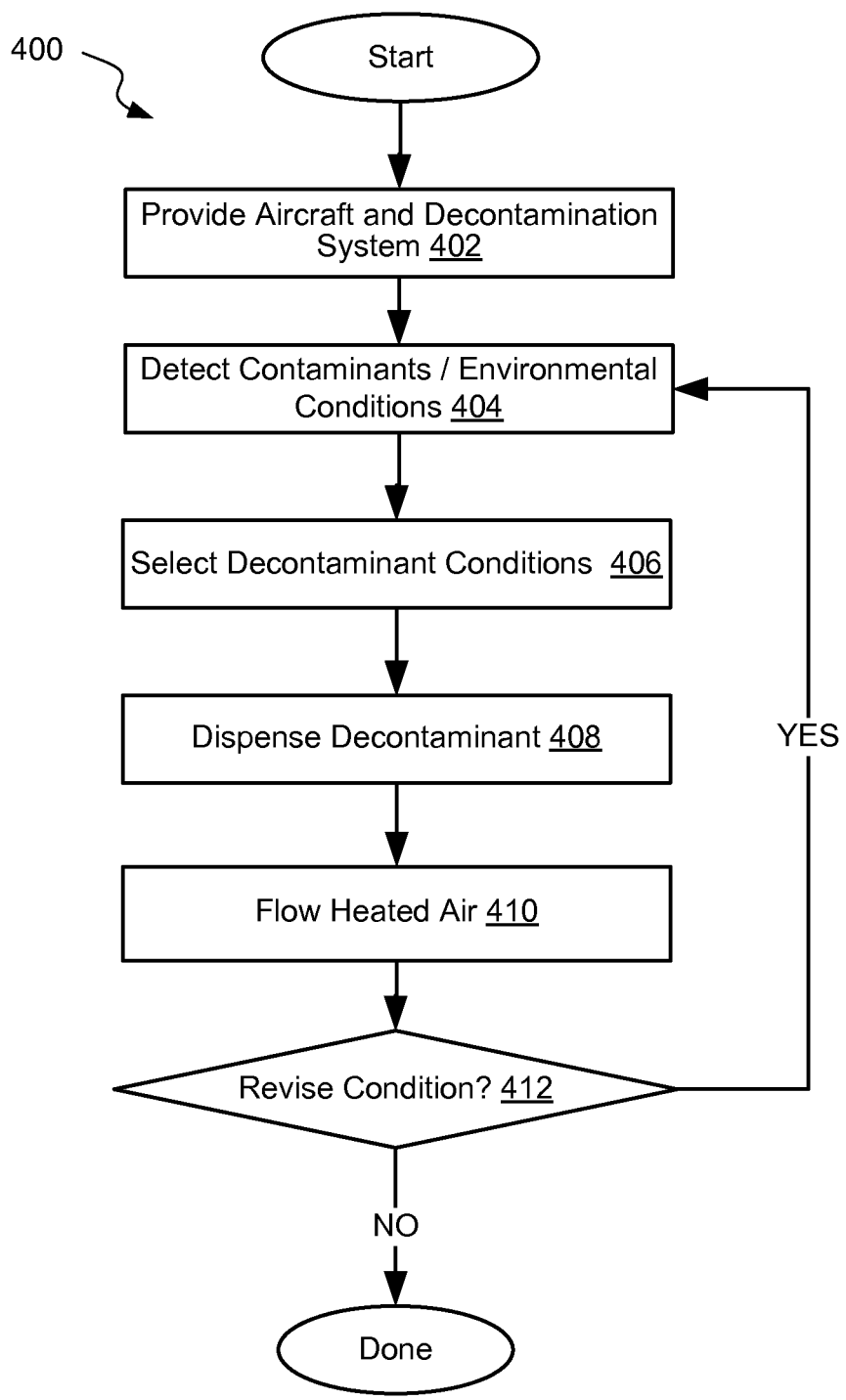
FIG. 4 is a process flowchart corresponding to a method for decontamination of an aircraft compartment, in accordance with some embodiments.

FIG. 4 is a process flowchart corresponding to a method 400 for decontamination of an aircraft compartment, in accordance with some embodiments. Method 400 may commence with providing an aircraft and a decontamination system during operation 402. Examples of aircrafts and decontamination systems are described elsewhere in this document. It should be noted that in some embodiments, the decontamination system may be a part of the aircrafts and no further operations are needed to functionally interconnect the two. For example, a decontaminating agent dispenser may be a cart that is stored on the aircraft and is rolled through an aisle during the dispensing operation. The air heater and air blower may be a part of the aircraft ventilation system. In other embodiments, at least some parts of the decontamination system may not be a part of the aircraft and certain functional connections are initially performed. For example, a decontaminating agent dispenser may be brought onto the aircraft compartment. Air ducts may be sealed against the doors of the aircraft if external air heaters and blowers are used.

Method 400 may proceed with detecting presence of one or more contaminants in the aircraft compartment during operation 404. Some examples of contaminants include target pathogens and bio-agents, such as viruses, bacteria, prions, and funguses. In addition to the contaminants' presence, operation 404 may involve detecting concentrations and other characteristics of these contaminants. Operation 404 may be performed manually by taking an air sample and/or a swipe sample and analyze these samples using various analytical techniques. This analysis is performed at the decontamination site and/or sent off-site for a more detailed analysis. The information about contaminant is then entered into the decontamination system using, for example, its input interface.

In some embodiments, the decontamination system may include one or more sensors capable of detecting presence of certain contaminants. This detection may be performed automatically, for example, after activating the system. The sensors may be configured to identify particular strains of the flu, the Ebola virus, tuberculosis, hemorrhagic fever, and/or any other contagion. Furthermore, an operator or other systems may supplement information about people previously present in the aircraft compartment (e.g., passengers), prior uses and/or locations of the aircraft, identify generalized symptoms of common infectious diseases without identifying a particular strain, and other like information. For example, the presence of an elevated body temperature, coughing, sweating, and other symptoms may indicate the presence of an infectious disease and may be supplied to the decontamination system for analysis.

In some embodiments, additional relevant information, such as the temperature and humidity inside the aircraft compartment as well as outside temperature and humidity, aircraft type and size, may be provided to the decontamination system during operation 404. Like the information about contaminants' presence, this additional information may be used for selecting appropriate decontamination conditions. Specifically, inside and outside temperature and humidity may be used to estimate heat dissipation and avoid having surfaces in the aircraft that are not sufficiently warm during the decontamination process, such as windows. The type of plane (e.g., commercial passenger plane, cargo plane, military) may restrict or allow using certain decontaminating agents. The size of the plane may be used to calculate the amount of decontaminating agents and hot air flow needed.

Method 400 may proceed with selecting decontamination conditions during operation 406. This selection is based on the information collected during operation 404, such as presence of one or more contaminants and, in some embodiments, other relevant information. A controller of the decontamination system may analyze this information using various algorithms and general information about contaminants, aircrafts, and the like. For example, the controller may be connected to a database with information about various contaminants and may extract specific information from this database relevant to the one or more contaminants detected in the aircraft compartment. Likewise, the controller may extract information about the aircraft. In some embodiments, the controller may connect to an external (to the decontamination system) network and obtain further information that may not be available. The aircraft communication system may be used for this purpose.

The decontamination conditions selected during operation 406 include at least identification of a decontaminating agent for dispending in an aerosolized form in the aircraft compartment, an operating temperature of a heated air for flowing through the aircraft compartment during the decontamination, and relative timing of dispensing the decontaminating agent and flowing the air. In some embodiments, other conditions may be used as well, such as humidity of the heated air, duration of the dispensing and flowing operations, and the like. For example, the conditions may specify a relative humidity for the heated to be between about 40% and 80%, such as about 60%. As noted above, the decontamination conditions may be different for different types of detected contaminants. Furthermore, the initial determined decontamination conditions can be later changed as further reflected by decision block 412.

The decontaminating agent selected during operation 406 may include one of more acids and/or one or more peroxides. For example, the decontaminating agent may include hydrogen peroxide. The concentration of hydrogen peroxide in the decontaminating agent may be less than 1% by weight and even less than 0.01% by weight. Hydrogen peroxide may be still effective at such low concentrations when combined with higher temperatures, such as between about 100 degrees Fahrenheit and 180 degrees Fahrenheit. In some embodiments, the decontaminating agent includes acetic acid. The concentration of the acetic acid may be may be less than 1% by weight and even less than 0.2% by weight.

In some embodiments, various pre-formulated decontaminating agents may be used, such as STERIPLEX™ HC solution available from SBIOMED LLC in Orem, Utah. STERIPLEX™ HC solution includes 0.03% by weight of silver, 19% by weight of glycerol, 0.0004% by weight of sorbitol, 10% by weight of ethanol, 0.03% of hydrogen peroxide, 0.25% by weight of peroxyacetic acid, 0.19% by weight of acetic acid, and 70% by weight of water. STERIPLEX™ HC solution or other like solutions may be diluted with water to less than 50% by weight of the solution, less than 30% by weigh, and even less than 20% by weight. The decontaminating agent may be supplied and, in some embodiments, formulated by the decontamination system.

The operating temperature of the heated air for flowing through the aircraft compartment during the decontamination may be between about 100 degrees Fahrenheit and 180 degrees Fahrenheit or, more specifically, between about 120 degrees Fahrenheit and 140 degrees Fahrenheit. This temperature may be specifically selected to increase efficacy of the decontaminating agent with respect to the detected contaminants. Other considerations for selecting a particular temperature or, more generally, a particular temperature profile is to minimize duration of the heated air flowing through the aircraft compartment and to minimize a concentration of the determined decontaminating agent.

In some embodiments, the temperature may be changed during the decontamination process as further described with reference to FIG. 5. In this situation, the decontamination conditions may include timing of the change and/or temperature ramping profile. In some embodiments, the temperature ramping profile is linear. For example, a lower initial temperature may be used to germinate spores, while a higher temperature may be later used together with the decontaminating agent to kill the spores.

After the decontamination conditions are selected during operation 406, method 400 may proceed with dispensing the decontaminating agent during operation 408 and flowing the air during operation 410. The combined duration of operations 408 and 410, including any repeats of these operations as indicated by decision block 412, may be less than 6 hours or, more specifically, less than 1 hour and even less than 15 minutes. Because the decontamination conditions are specifically tailored and profiled for the defected contaminants, the effective decontamination may be achieved within a relatively short period of time. In some embodiments, more than 95% of detected contaminants are removed or inactivated after completing method 400 or, more specifically, more than 99% and even more than 99.9%.

The relative timing of dispensing the decontaminating agent (i.e., operation 408) and flowing the air (i.e., 410) is another decontamination condition selected during operation 406. In some embodiments, operation 408 starts before operation 410. Operation 408 may be completed before the start of operation 410 or there may be some overlap between these operations. In some embodiments, operation 408 may be repeated one or more times while operation 410 continues. Alternatively, operation 410 may start before operation 408. Operation 410 may continue while operation 408 is performed. In some embodiments, one or more parameters of operation 408 and/or operation 410 are changed while these operations continue or repeated. Some of these examples will now be described with reference to FIG. 5.

Figure 5:
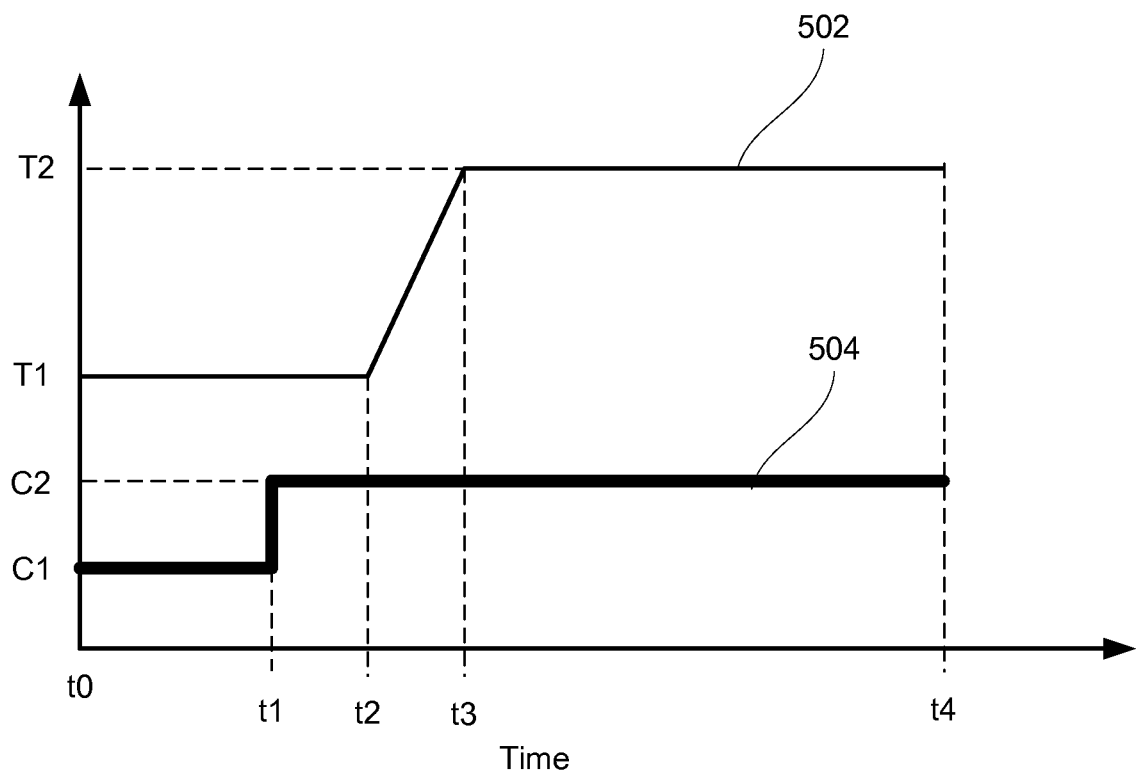
FIG. 5 is a schematic representation of a temperature profile and a concentration profile during a decontamination process, in accordance with some embodiments.

Specifically, FIG. 5 is a schematic representation of a temperature profile 502 and a concentration profile 504 during a decontamination process as functions of time, in accordance with some embodiments. The decontamination process may start at time 0, which corresponds to a certain concentration (C1) of the decontaminating agent and a certain temperature (T1) of the air flown into the aircraft compartment. In some embodiments, the decontaminating agent is not introduced into the compartment until later time (e.g., t1) and the initial concentration of the agent (between t0 and t1, i.e., concentration C1) may be about zero. In other embodiments, some decontaminating agent is introduced into the compartment at the beginning of the decontamination process (t0). This concentration may be significantly lower than conventionally used concentrations of decontaminating agents. For example, the decontamination agent may be hydrogen peroxide and the initial concentration may be less than 1% by weight or even less than 0.01% by weight. The initial temperature (T1) may be higher than the room temperature and, in some embodiments, may be between about 90 degrees Fahrenheit and 160 degrees Fahrenheit or, more specifically, between about 100 degrees Fahrenheit and 140 degrees Fahrenheit or even between about 100 degrees Fahrenheit and 120 degrees Fahrenheit. As noted above, the conditions during this initial period may be specifically selected to stimulate germination of spores because the germinating spores are significantly less resilient to decontaminating agents than the intact spores.

At some point in time (t1), the concentration of the decontaminating agent is increased to a new level (C2) that is higher than the initial concentration (C1). For example, the same but a more concentrated decontaminating agent may be dispensed at t1 (in comparison to t0) or additional decontaminating agent may be added. The decontaminating agent at the new concentration (C2) is dispensed in preparation for killing the germinating spores. It should be noted that the concentration needed to kill germinating spores is significantly lower than the concentration required for killing an intact spore and C2 may be still substantially lower than conventionally used concentrations of decontaminating agents. For example, less than 1% by weight of hydrogen peroxide or even less than 0.01% by weight may be dispensed in the aerosolized form at this stage. A ratio of the new concentration to the original concentration (i.e., C2/C1) may at least about 2, at least about 5, at least about 10, and even at least about 100.

At time t2, the temperature may start being ramped up to a new higher level (T2). It should be noted that this new temperature level (T2) is still lower than the conventionally used thermal decontamination (e.g., the method using hot humid air). For example, the new temperature (T2) may be between about 100 degrees Fahrenheit and 180 degrees Fahrenheit or, more specifically, between about 120 degrees Fahrenheit and 160 degrees Fahrenheit or even between about 130 degrees Fahrenheit and 140 degrees Fahrenheit. Like the conditions used during the initial period (t0-t1), this temperature (T2) may be selected for specific contaminants detected earlier. In some embodiments, the difference between the new temperature (T2) and the initial temperature (T1) may be between about 10 degrees Fahrenheit and 50 degrees Fahrenheit or, more specifically, between 20 degrees Fahrenheit and 40 degrees Fahrenheit.

At time t3, the temperature reaches the new level (T2). The temperature ramp-up may follow a linear profile (as shown in FIG. 5), exponential profile, step-profile, and other types of profiles. The average temperature ramp-up rate may be between about 1 degree Fahrenheit per minute and 20 degrees Fahrenheit per minute during the t2=>t3 period. The duration of this temperature ramp-up period and/or the temperature profile may be specifically selected to increase efficacy of the decontaminating agent with respect to the detected contaminants. As the temperature increases, the efficacy of the decontaminating agent is enhanced until it becomes offset due to evaporation and dissociation of the decontaminating agent. In some embodiments, the decontamination process also involves maintaining a certain humidity profile (not shown in FIG. 5) in the aircraft compartment to better control the evaporation and/or dissociation. After the temperature ramp-up, the temperature may be maintained at the new level (T2) to evaporate the decontaminating agent.

Returning to FIG. 4, operation 408 involves dispensing the decontaminating agent in an aerosolized form in the aircraft compartment using, for example, aerosol spraying equipment, atomizer nozzle, nebulizer, electrospray, and vibrating orifice aerosol generator (VOAG). One example of such equipment is described above with reference to FIG. 3. This equipment may be in the form of a mobile station that can be rolled through the aircraft compartment to ensure uniform distribution of the decontaminating agent. In other embodiments, the aerosol equipment may be integrated into ventilation equipment and operations 408 and 410 may partially or completely overlap. Operation 408 may also involve formulating the decontaminating agent.

The size of the aerosol droplets discharged from the equipment may be selected based at least on a viscosity of the decontaminating agent, an ability of the decontaminating agent to retain a charge (if electrostatic features are used), a desired volatility (i.e., evaporating time) of the decontaminating agent, a temperature within the aircraft compartment and. In some embodiments, the size of the aerosol droplets is between about 1 micron and 20 microns on average.

Operation 410 involves flowing the heated air through the aircraft compartment at the operating temperature. Air heaters and blowers may be used for this operation as described above.

In some embodiments, one or more operations 404-410 are repeated using the same or different conditions as reflected by decision block 412. For example, the decontamination process may involve a feedback control loop for monitoring various parameters, such as presence of contaminants in the aircraft cabin, concentration of the decontaminating agent, air temperature in the aircraft compartment, and the like. For example, presence of the contaminants may be checked one or more additional times to ensure effectiveness of the decontamination process. The decontamination conditions may be changed during the process as, for example, described above with reference to FIG. 5.

Examples of Aircrafts

Figure 6A:
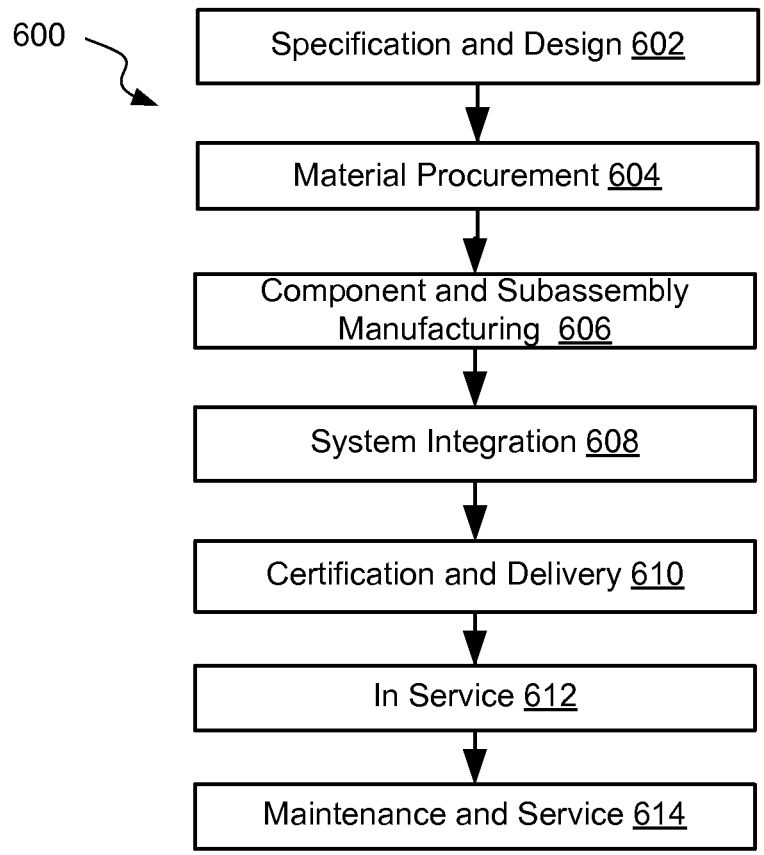
FIG. 6A is a process flowchart reflecting key operations in aircraft manufacturing and service, in accordance with some embodiments.

An aircraft manufacturing and service method 600 shown in FIG. 6A and an aircraft 630 shown in FIG. 6B will now be described to better illustrate various features of decontamination processes and systems presented herein. During pre-production, aircraft manufacturing and service method 600 may include specification and design 602 of aircraft 630 and material procurement 604. The production phase involves component and subassembly manufacturing 606 and system integration 608 of aircraft 630. Thereafter, aircraft 630 may go through certification and delivery 610 in order to be placed in service 612. While in service by a customer, aircraft 630 is scheduled for routine maintenance and service 614 (which may also include modification, reconfiguration, refurbishment, and so on). While the embodiments described herein relate generally to servicing of commercial aircraft, they may be practiced at other stages of the aircraft manufacturing and service method 600. For example, a decontamination process may be implemented at various stages of aircraft production as many people have access to an aircraft and its components during a production process.

Each of the processes of aircraft manufacturing and service method 600 may be performed or carried out by a system integrator, a third party, and/or an operator (e.g., a customer). For the purposes of this description, a system integrator may include, without limitation, any number of aircraft manufacturers and major-system subcontractors; a third party may include, for example, without limitation, any number of venders, subcontractors, and suppliers; and an operator may be an airline, leasing company, military entity, service organization, and so on.

Figure 6B:
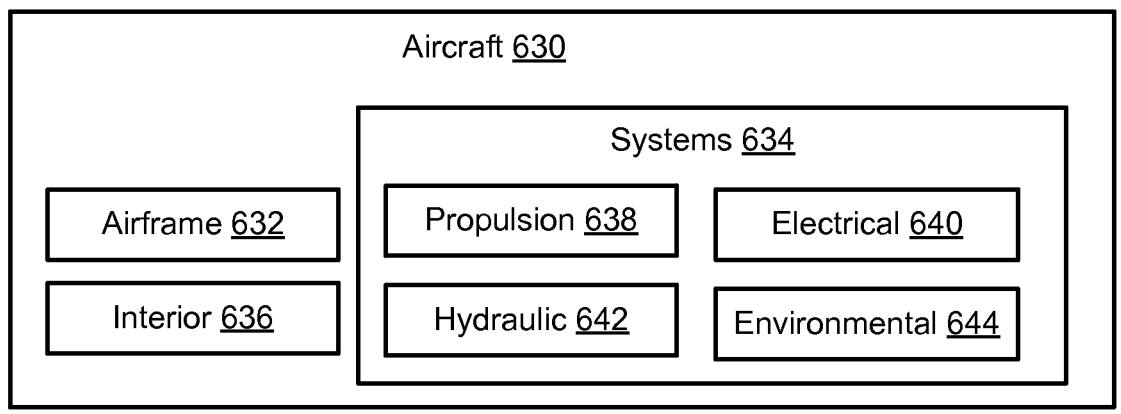
FIG. 6B is a block diagram illustrating various key components of an aircraft, in accordance with some embodiments.

As shown in FIG. 6B, aircraft 630 produced by aircraft manufacturing and service method 600 may include airframe 632, interior 636, and multiple systems 634 and interior 636. Examples of systems 634 include one or more of propulsion system 638, electrical system 640, hydraulic system 642, and environmental system 644. Any number of other systems may be included in this example. Although an aircraft example is shown, the principles of the disclosure may be applied to other industries, such as the automotive industry.

Apparatus and methods embodied herein may be employed during any one or more of the stages of aircraft manufacturing and service method 600. For example, without limitation, components or subassemblies corresponding to component and subassembly manufacturing 606 may be fabricated or manufactured in a manner similar to components or subassemblies produced while aircraft 630 is in service.

Also, one or more apparatus embodiments, method embodiments, or a combination thereof may be utilized during component and subassembly manufacturing 606 and system integration 608, for example, without limitation, by substantially expediting assembly of or reducing the cost of aircraft 630. Similarly, one or more of apparatus embodiments, method embodiments, or a combination thereof may be utilized while aircraft 630 is in service, for example, without limitation, to maintenance and service 614 may be used during system integration 608 and/or maintenance and service 614 to determine whether parts may be connected and/or mated to each other.

Examples of Controller Computer Systems

Figure 7:
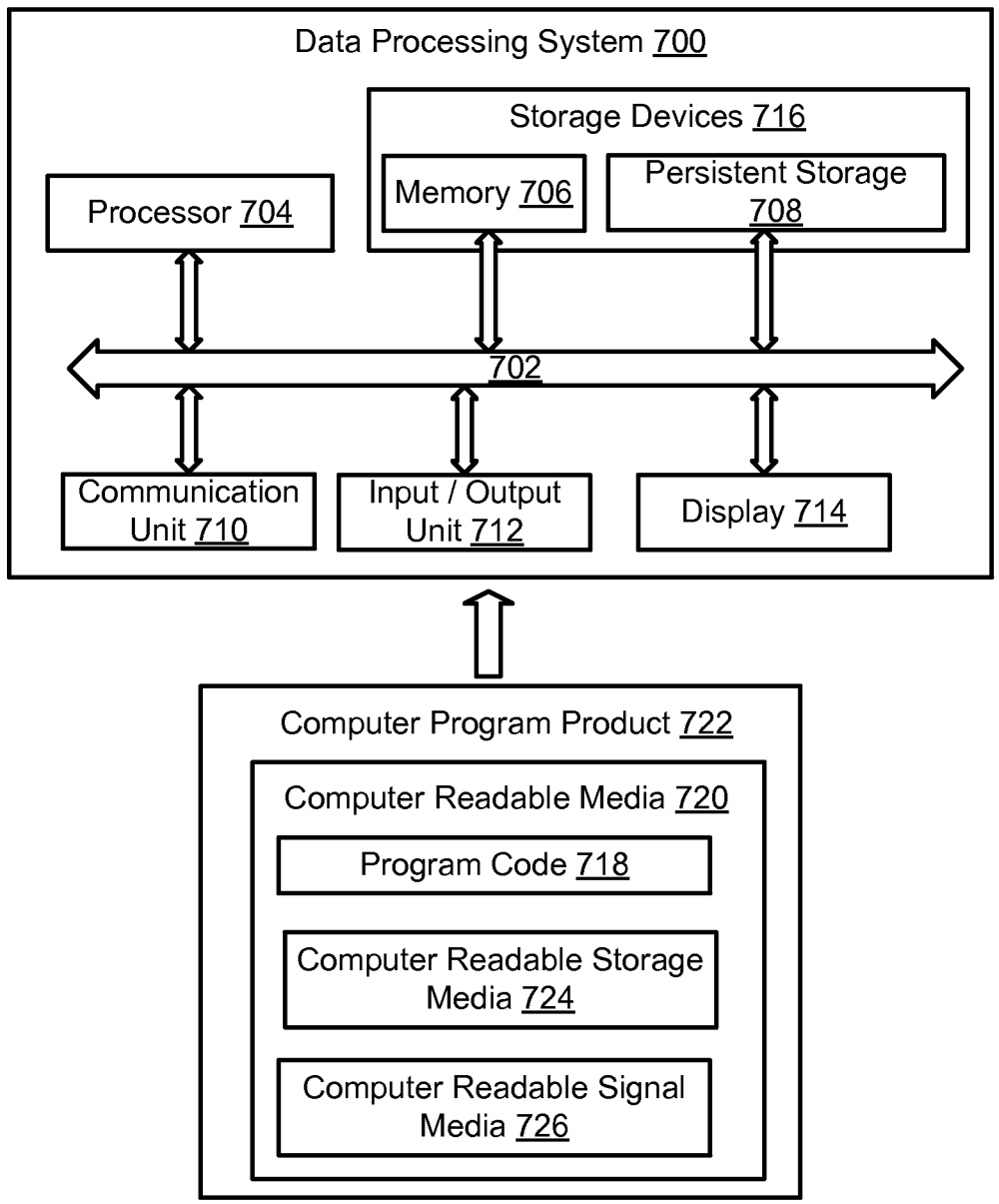
FIG. 7 is a block diagram illustrating a data processing system, in accordance with some embodiments.

Turning now to FIG. 7, an illustration of a data processing system 700 is depicted in accordance with some embodiments. Data processing system 700 may be used to implement one or more computers used in a controller or other components of decontamination systems described above. In some embodiments, data processing system 700 includes communications framework 702, which provides communications between processor unit 704, memory 706, persistent storage 708, communications unit 710, input/output (I/O) unit 712, and display 714. In this example, communications framework 702 may take the form of a bus system.

Processor unit 704 serves to execute instructions for software that may be loaded into memory 706. Processor unit 704 may be a number of processors, a multi-processor core, or some other type of processor, depending on the particular implementation.

Memory 706 and persistent storage 708 are examples of storage devices 716. A storage device is any piece of hardware that is capable of storing information, such as, for example, without limitation, data, program code in functional form, and/or other suitable information either on a temporary basis and/or a permanent basis. Storage devices 716 may also be referred to as computer readable storage devices in these illustrative examples. Memory 706, in these examples, may be, for example, a random access memory or any other suitable volatile or non-volatile storage device. Persistent storage 708 may take various forms, depending on the particular implementation. For example, persistent storage 708 may contain one or more components or devices. For example, persistent storage 708 may be a hard drive, a flash memory, a rewritable optical disk, a rewritable magnetic tape, or some combination of the above. The media used by persistent storage 708 also may be removable. For example, a removable hard drive may be used for persistent storage 708.

Communications unit 710, in these illustrative examples, provides for communications with other data processing systems or devices. In these illustrative examples, communications unit 710 is a network interface card.

Input/output unit 712 allows for input and output of data with other devices that may be connected to data processing system 700. For example, input/output unit 712 may provide a connection for user input through a keyboard, a mouse, and/or some other suitable input device. Further, input/output unit 712 may send output to a printer. Display 714 provides a mechanism to display information to a user.

Instructions for the operating system, applications, and/or programs may be located in storage devices 716, which are in communication with processor unit 704 through communications framework 702. The processes of the different embodiments may be performed by processor unit 704 using computer-implemented instructions, which may be located in a memory, such as memory 706.

These instructions are referred to as program code, computer usable program code, or computer readable program code that may be read and executed by a processor in processor unit 704. The program code in the different embodiments may be embodied on different physical or computer readable storage media, such as memory 706 or persistent storage 708.

Program code 718 is located in a functional form on computer readable media 720 that is selectively removable and may be loaded onto or transferred to data processing system 700 for execution by processor unit 704. Program code 718 and computer readable media 720 form computer program product 722 in these illustrative examples. In one example, computer readable media 720 may be computer readable storage media 724 or computer readable signal media 726.

In these illustrative examples, computer readable storage media 724 is a physical or tangible storage device used to store program code 718 rather than a medium that propagates or transmits program code 718.

Alternatively, program code 718 may be transferred to data processing system 700 using computer readable signal media 726. Computer readable signal media 726 may be, for example, a propagated data signal containing program code 718. For example, computer readable signal media 726 may be an electromagnetic signal, an optical signal, and/or any other suitable type of signal. These signals may be transmitted over communications links, such as wireless communications links, optical fiber cable, coaxial cable, a wire, and/or any other suitable type of communications link.

The different components illustrated for data processing system 700 are not meant to provide architectural limitations to the manner in which different embodiments may be implemented. The different illustrative embodiments may be implemented in a data processing system including components in addition to and/or in place of those illustrated for data processing system 700. Other components shown in FIG. 7 can be varied from the illustrative examples shown. The different embodiments may be implemented using any hardware device or system capable of running program code 718.

CONCLUSION

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present embodiments are to be considered as illustrative and not restrictive.

What is claimed is:

1. A method for decontamination of a compartment, the method comprising:
   detecting presence of one or more contaminants;
   selecting decontamination conditions for use in the compartment based on the presence of the one or more contaminants in the compartment,
      the decontamination conditions comprise at least a decontaminating agent for dispending in an aerosolized form in the compartment, an operating temperature of a heated air for flowing through the compartment during the decontamination, a relative humidity of the heated air flowing through the compartment, and a relative timing of dispensing the decontaminating agent and flowing the heated air, wherein the relative humidity of the heated air is between 40% and 80%;
   dispensing the decontaminating agent in the aerosolized form in the compartment; and
   flowing the heated air through the compartment at the operating temperature,
      wherein the operating temperature is selected for efficacy of the decontaminating agent with respect to the one or more contaminants, and wherein the decontaminating agent is dispensed prior to flowing the heated air through the compartment at the operating temperature.

2. The method of claim 1, wherein the operating temperature is between about 100 degrees Fahrenheit and 180 degrees Fahrenheit.

3. The method of claim 1, wherein the operating temperature is between about 120 degrees Fahrenheit and 140 degrees Fahrenheit.

4. The method of claim 1, wherein the operating temperature is selected to minimize duration of the heated air flowing through the compartment.

5. The method of claim 1, wherein the operating temperature is selected to minimize a concentration of the decontaminating agent.

6. The method of claim 1, wherein the decontaminating agent comprises hydrogen peroxide and acetic acid.

7. The method of claim 6, wherein a concentration of hydrogen peroxide in the decontaminating agent is less than 1% by weight.

8. The method of claim 6, wherein a concentration of hydrogen peroxide in the decontaminating agent is less than 0.01% by weight.

9. The method of claim 1, wherein the decontamination conditions further comprise a temperature ramping profile.

10. The method of claim 9, wherein the temperature ramping profile is linear.

11. The method of claim 1, wherein the decontaminating agent is dispensed after flowing the heated air through the compartment at the operating temperature.

12. The method of claim 1, wherein the decontaminating agent in the aerosolized form comprises droplets that are between about 1 micron and 20 microns in size.

13. The method of claim 1, further comprising providing a decontamination system,
   the decontamination system comprising a decontaminating agent dispenser, an air heater, an air blower, and a controller,
   the controller being configured to determine the decontamination conditions.

14. The method of claim 13, wherein at least a portion of the decontamination system is integrated into an aircraft.

15. The method of claim 13, wherein at least a portion of the decontamination system is separate from an aircraft.

16. The method of claim 13, wherein the decontamination system further comprises one or more sensors for determining presence of the one or more contaminants.

* * * * *